ACOUSTIC POLARIMETER

United States Patent [19]
Rouge et al.

[11] 4,367,649
[45] Jan. 11, 1983

[54] ACOUSTIC POLARIMETER

[75] Inventors: Jean Rouge; André Robert, both of Paris, France

[73] Assignee: Thomson-CSF, Paris, France

[21] Appl. No.: 228,622

[22] Filed: Jan. 26, 1981

[30] Foreign Application Priority Data

Jan. 29, 1980 [FR] France .................. 80 01895

[51] Int. Cl.³ .............................. G01N 29/00
[52] U.S. Cl. ................. 73/645; 73/589; 73/644
[58] Field of Search .......... 73/645, 589, 618, 620, 73/624, 642, 644, 646, 647, 648

[56] References Cited

U.S. PATENT DOCUMENTS 4,138,894  2/1979  Robert et al. ............ 73/645 X

FOREIGN PATENT DOCUMENTS 2069697  8/1981  United Kingdom .......... 73/589

OTHER PUBLICATIONS

Optical Heterodyne Method for Measuring Mechanical Oscillation, by Pushert, Feinwerktechnik & Messtechnik 83 (1975), No. 7, pp. 316/317.

Primary Examiner—Edward R. Kazenske
Assistant Examiner—David V. Carlson
Attorney, Agent, or Firm—Oblon, Fisher, Spivak, McClelland & Maier

[57] ABSTRACT

An acoustic polarimeter for measuring the anisotropy of a sample comprises an electroacoustic transducer which transmits a high-frequency transverse acoustic wave and is fixed on a birefringent measuring plate. The acoustic wave is received by a second transducer and this latter is sensitive to the component of the wave which is parallel to the transmitted wave. Transmission devices are provided for delivering electrical signals which are frequency-modulated about a tunable mean frequency. The electrical signals applied to the second transducer are received on a zero indicator, thus permitting determination of the directions of the slow axis and fast axis of the sample as well as the angle of phase shift introduced by the sample.

9 Claims, 4 Drawing Figures

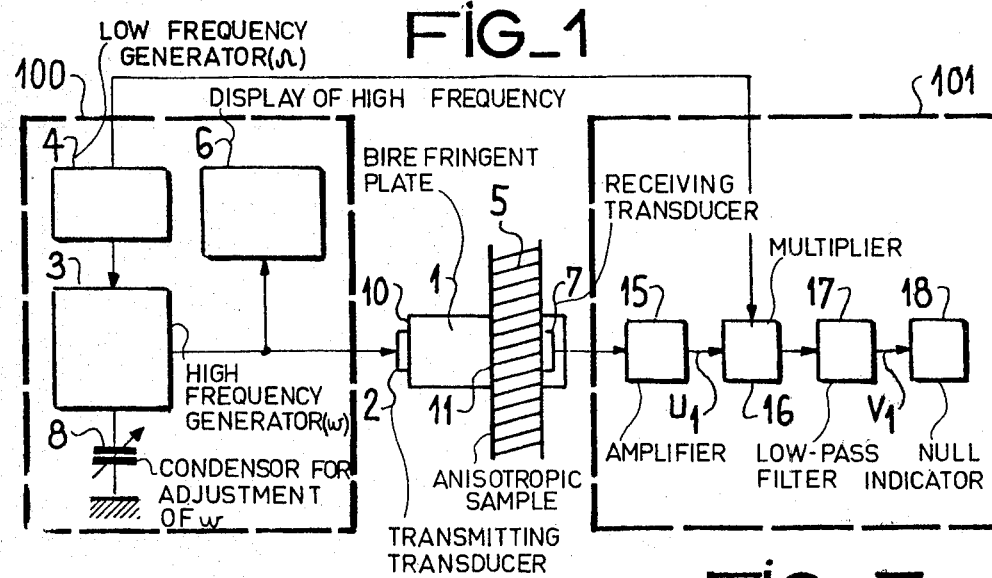

ACOUSTIC POLARIMETER

BACKGROUND OF THE INVENTION

1. Field of the Invention

This invention relates to an acoustic polarimeter for measuring the anisotropy of a solid by determining its acoustic birefringence, the anisotropy being induced by an acoustic stress, for example.

2. Description of the Prior Art

It is known that, if a linearly polarized acoustic wave is applied to the input of an anisotropic solid, the output wave usually has elliptical polarization. This ellipticity depends on the phase shift of the wave between the wave components along the two related orthogonal axes, namely the slow axis and the fast axis. The ellipticity also depends on the angle made by the initial polarization with the slow and fast axes.

A measurement of polarization therefore involves the determination of the slow and fast axes and the phase shift introduced by the solid in respect of the components along these two axes.

It is known to measure with a probe comprising an electroacoustic transducer which transmits the polarized acoustic wave and coupled to a generator for producing electrical signals at a frequency which can be varied either continuously or periodically. The probe being provided in addition with an auxiliary birefringent plate placed behind the emitting transducer and an assembly comprising two electroacoustic transducers which are sensitive respectively to the polarization components located at 45° to each other.

The solid to be measured being introduced between the auxiliary birefringent plate and the assembly of receiving transducers. The probe unit being orientable and the solid-polarization parameters measured by means of signals delivered successively by the two receiving transducers.

The disadvantage attached to the polarimeter in accordance with the prior art lies in the fact that it entails the need for two receiving transducers which cannot be aligned simultaneously with respect to the incident wave; this is liable to give rise to errors in the determination of parameters.

SUMMARY OF THE INVENTION

The polarimeter in accordance with the invention overcomes this disadvantage by virtue of the fact that it comprises only one transducer which is aligned with respect to the incident wave.

In brief outline, the acoustic polarimeter aforesaid serves to measure the anisotropy of a sample having substantially parallel faces, thereby permitting determination of the directions of the fast axis $O\xi$ and of the slow axis $O\eta$, as well as the phase-shift angle $\Phi_0$ at a frequency $\omega_0/2\pi$ between the components of a transverse acoustic wave along the axes $O\xi$ and $O\eta$, this wave having passed through the sample at right angles to its faces. The polarimeter comprises a birefringent plate for measuring the fast axis $Ox_1$ and the slow axis $Oy_1$, an electroacoustic transducer which is fixed on one face of the birefringent plate whose opposite face can be placed in contact with the entrance face of the sample. The transducer transmits acoustic waves with are polarized substantially along an axis $Ox_2$ located at 45° with respect to the fast axis $Ox_1$ of the plate and is connected to means (100) for generating high-frequency electrical signals having an angular frequency $\omega$ which can be varied manually and/or frequency-modulated at the low-frequency pulsatance $\Omega$. The polarimeter is distinquished by the fact that the waves which have passed through the sample are received by a single transducer fixed on a support frame and applied against the exit face of the sample, that the transducer is sensitive only to the component of the acoustic wave along the axis $Ox_2$, that the assembly formed by the transmitting transducer, the measuring plate and the support frame of the receiving transducer is capable of rotating as a single unit about the axis $Oz$ in an arrangement designated as a "probe", that the electrical signals delivered by the receiving transducer are applied to receiving circuits and that a signal produced at the output of said circuits is applied to a zero indicator. In the case of an angular frequency $\omega = \omega_0$ of the wave, a zero measurement read on the indicator is obtained if the angle between the axis $O\xi$ or the axis $O\eta$ and the axis $Ox_2$ is zero, thus determining the orientation of the axis $O\xi$ to within 90°. After rotation of the probe through an angle of 45° and by varying the value of angular frequency of the wave, the direction of variation on the zero indicator gives the sign of the phase shift $\Phi_0$ and the discrimination between slow axis and fast axis of the sample; the value $\Phi_0$ is obtained from the values $\omega_0$ and $\omega_1$ at which the indicator is again at zero.

BRIEF DESCRIPTION OF THE DRAWINGS

These and other features of the invention will be more apparent upon consideration of the following description and accompanying drawings, in which:

FIG. 1 is a general diagram of the polarimeter in accordance with the invention;

FIG. 2 illustrates the probe comprising one of the transmitting and receiving transducers and a birefringent plate;

FIG. 3 illustrates the mechanical assembly of the probe;

FIG. 4 shows the relative positions of the fast axes of the birefringent plate, of the sample and the direction of emission.

DETAILED DESCRIPTION OF THE PREFERRED EMBODIMENTS

FIG. 1 shows diagrammatically one exemplified embodiment of a polarimeter in accordance with the invention for measuring the anisotropy parameters of a solid 5 sample having substantially parallel faces. The solid 5 can be introduced into a unit designated as a measuring probe. This probe unit is composed of an acoustically birefringent plate 1 having two parallel end faces, the fast and slow orthogonal axes of said plate being perpendicular to the direction of propagation of the acoustic waves. On one face 10 designated as an "entrance face", there is fixed at least one transducer 2 which transmits linearly polarized transverse acoustic waves, the axis of polarization being oriented at 45° to the fast axis of the plate 1. The sample 5 to be studied is applied on the other face 11 which is designated as the "exit face". If the polarimeter operates in the transmission mode, the transducer which receives the acoustic waves after these latter have passed through the sample along a simple path is applied on the sample face located opposite to the face on which the output face of the plate is applied. Thus the axis of polarization of the transducer 7 is oriented parallel to the axis of polarization of the transmitting transducer 2 or in other words at 45° with respect to the fast axis of the plate 1.

In an alternative embodiment of the invention, the polarimeter operates in reflection from the rear face of the sample. In this case, the transducer 2 is operated successively in the switching, transmitting and receiving modes.

The transmitting unit 100 comprises a high-frequency signal generator 3. The angular frequency $\omega$ of said signals can be adjusted manually by means of a variable capacitor 8, for example. Moreover, the generator 3 can be frequency-modulated at the pulsatance $\Omega$ delivered by a low-frequency generator 4.

Typical examples of the frequencies adopted are as follows: $\omega/2\pi = 2$ MHz and $\Omega/2\pi = 100$ Hz. In a preferential embodiment, the generator 3 comprises a chopper amplifier.

A frequency meter 6 serves to display the frequency. The receiving unit 101 is also shown in FIG. 1.

The electrical signals delivered by the receiving transducer 7 for the polarimeter in the transmission mode or the tramsducer 2 which is switched to the receiving mode for the polarimeter in the reflecting mode are amplified by the amplifier 15, multiplied in the multiplier circuit 16 by the sine-wave signal at the angular frequency $\Omega$ delivered by the generator 4. At the output of the multiplier circuit 16, the signal is filtered by the low-pass filter 17 and applied to a null indicator 18.

The assembly formed by the birefringent plate 1 with the transmitting transducer 2 and the support frame comprising the receiving transducer for the transmission polarimeter can be rotated about the axis Oz of the direction of propagation. This rotation is indicated at 19 with respect to the sample which does not rotate.

Said probe is shown in FIG. 2 in which the directions $Ox_1$ and $Oy_1$ respectively of the fast axis and of the slow axis of the plate 1 are indicated. The transmitting transducer transmits polarized waves along the axis $Ox_2$ which is located at an angle of 45° with respect to the axis $Ox_1$. The receiving transducer 7 receives the acoustic-wave components which are parallel to the axis $Ox_2$.

FIG. 3 shows one example of construction of the mechanical support frame. The birefringent plate together with the emitting transducer 2 and the frame of the receiving transducer 7 are mounted on two variably spaced members 31 and 32. This makes it possible to place the receiving transducer 7 in contact with the exit face of the birefringent plate 1 and to interpose the sample 5. The angle of rotation $\theta$ which is smaller than 120° is indicated on a cylindrical surface having an axis Oz.

When the sample 5 is not present, the high-frequency generator 3 is adjusted by means of the control element 8 so as to deliver a pulsating current having a mean value of angular frequency $\omega_0$ such that the phase shift $\psi_0$ of the birefringent plate has the value:

$$\psi_0 = (2k+1)\pi \qquad (1)$$

Where k is integer, the exit face of the plate 1 is in contact with the receiving transducer 7 and $\omega$ assumes the value $\omega_0$ when the null indicator is in fact at zero. There is then introduced the sample 5 in which the directions of the fast and slow axes $O\xi$ and $O\eta$ are to be determined. Referring to FIG. 4, $\theta$ designates the angle between the axes $Ox_1$ and $O\xi$. In the absence of frequency modulation of the generator 3, the voltage obtained at the input of the multiplication circuit 16 is given by $U_1$, $\Phi_0$ being the phase shift introduced by the sample:

$$U_1 = \qquad (2)$$
$$U_0 \sqrt{1 + \sin^2 2\theta \cos\psi_0 + \cos 2\theta(\cos 2\theta \cos\Phi_0 \cos\psi_0 - \sin\Phi_0 \sin\psi_0)}$$

where $U_0$ is a constant which is proportional to the amplitude of the transmitted waves.

When the fast axis of the sample is oriented in a direction parallel to the axis $Ox_2$, the angle $\theta$ is equal to $\pm\pi/4$. In this case, the voltage $U_1$ is given by:

$$U_1 = U_0 \sqrt{1 + \cos\psi_0} = 2U_0 \left| \cos\frac{\psi_0}{2} \right| \qquad (3)$$

In accordance with expression (1), the volatage $U_1$ is zero and could therefore be read on a zero indicator placed next in succession to the circuit 15. In order to improve accuracy of measurement, the polarimeter makes use of a zero method involving modulation of the transmitted acoustic wave having an angular frequency $\omega$ by the lower value of angular frequency $\Omega$, with the result that:

$$\omega = \omega_0(1 + \epsilon_0 + \epsilon_1 \sin \Omega t) = \omega_0 A \qquad (4)$$

where, for the purpose of finding the axes of anisotropy of the sample, $\epsilon_0 = 0$.

The phase shifts $\psi$ and $\Phi$ of the plate 1 and of the sample having an angular frequency $\omega$ are expressed by:

$$\psi = A\psi_0 \text{ and } \Phi = A\Phi_0 \qquad (5)$$

Postulating that $\psi_1 = \psi_0 \epsilon_1$ and taking into account the expressions (1), (4) and (5), the voltage $U_1$ which is given by expression (3) and in which $\psi_0$ is replaced by $\psi$ becomes at the output of the multiplier 16:

$$V_1 = V_0 \left| 2 J_1\left(\frac{\psi_1}{2}\right) \sin\Omega t \right| \times \sin\Omega t \qquad (6)$$

by utilizing a series development of Bessel functions at the fondamental frequency, $V_0$ being proportional to $U_0$.

The mean value of this voltage obtained by means of the low-pass filter 17 is zero as a function of time. Determination of the axes of anisotropy of the sample is then carried out by rotational displacement of the probe about the axis of propagation of the acoustic waves until the voltage read on the indicator 18 is reduced to zero: in this position $\theta = \pm\pi/4$ indicated by a line 19 cut on the probe, the axes of anisotropy of the sample are at $\pi/4$ with respect to the axes of anisotropy of the plate 1. Coincidence of the axes is then obtained by producing a rotation of $\pi/4$ of the probe either in one direction or in the other so as to permit measurement of the anisotropy phase-shift in the sample.

Since the direction of the axes of the sample 5 is known, it still remains necessary to determine its phase shift $\Phi_0$ at the angular frequency $\omega_0$.

The rotation of $\pi/4$ of the probe in either one direction or the other with respect to the position obtained which corresponds to the direction $\theta = \pm \pi/4$ makes it possible to obtain either $\theta = 0$ or $\theta = \pi/2$.

The voltage $U_1$ given by the expression (2) in which $\Psi_0$ and $\Phi_0$ are replaced by $\Psi$ and $\Phi$ in accordance with the equations (5) becomes:

$$U_1 = 2U_0 \left| \cos\left(\frac{\psi \pm \Phi}{2}\right) \right| \quad (7)$$

Taking into account the expressions (1), (4) and (5) and postulating that $$\Psi_2 = (\Psi_0 \pm \Phi_0)\epsilon_1$$

the voltage obtained at the output of the multiplier 16 is equal to:

$$V_1 = V_0 \left| \sin\left[(2k+1)\frac{\pi\epsilon_0}{2} \pm \frac{\Phi_0}{2}(1+\epsilon_0) + \frac{\psi_2}{2} \sin \Omega t \right] \right| \times \sin \Omega t \quad (8)$$

The mean value of this voltage read on the indicator 18 is zero in respect of $$(2k+1)\frac{\pi\epsilon_0}{2} \pm \frac{\Phi_0}{2}(1+\epsilon_0) = 0$$

whence:

$$\Phi_0 = \pm (2k+1)\pi \frac{\omega_0 - \omega_1}{\omega_1} \text{ with } \omega_1 = \omega_0(1+\epsilon_0) \quad (9)$$

The value of phase shift $\Phi_0$ of the sample is therefore obtained from the value $\omega_1$, this latter being obtained by means of the control element 8 so as to vary the frequency of the generator 3 until the voltage read on the indicator 18 is reduced to zero.

If the voltage is reduced to zero with $\Phi_0 > 0$, the fast axis of the sample is parallel to the reference direction $Ox_1$; in this case and in accordance with expression (9), the angular frequency $\omega_1$ is lower than $\omega_0$ and $\theta = 0$. On the other hand, if the voltage is reduced to zero with $\Phi_0 < 0$, the slow axis of the sample is parallel to $Ox$, the angular frequency $\omega_1$ is higher than $\omega_0$ and $\theta = \pi/2$.

In the case of the reflection method, the procedure is identical except for the fact that all the phase shifts are duplicated; in order to ensure that the birefringent plate performs the same function as in transmission, $\Psi_0$ must be divided by 2.

There has thus been described an acoustic polarimeter which provides measurements of acoustic birefringence with enhanced accuracy and greater simplicity than the polarimeters which were known in the prior art.

What is claimed is:

1. An acoustic polarimeter for measuring the anisotropy of a sample having substantially parallel faces so as to permit determination of the directions of the fast axis $O\xi$ and of the slow axis $O\eta$ as well as the phase-shift angle $\phi_0$ at a frequency $\omega_0/2\pi$ between the components of a transverse acoustic wave along the axes $O\xi$ and $O\eta$, said wave having passed through the sample at right angles to its faces, the polarimeter comprising a birefringent plate for measuring the fast axis $Ox_1$ and slow axis $Oy_1$, an electroacoustic transducer which is fixed on one face of the birefringent place whose opposite face can be placed in contact with the entrance face of the sample, said transducer transmitting acoustic waves which are polarized substantially along an axis $Ox_2$ located at 45° with respect to the fast axis $Ox_1$ of the plate and said transducer being connected to means for generating high-frequency electrical signals having an angular frequency $\omega$ which can be varied manually and/or frequency-modulated at the low frequency pulsatance $\Omega$, wherein the waves which have passed through the sample are received by a single transducer fixed on a support frame and applied against the exit face of the sample, wherein the receiving transducer is sensitive only to the component of the acoustic wave along the axis $Ox_2$, wherein the assembly formed by the transmitting transducer, the measuring plate and the support frame of the receiving transducer is capable of rotating as a single unit about the axis $Oz$ in an arrangement designated as a "probe", wherein the electrical signals delivered by the receiving transducer are applied to receiving circuits, a signal delivered at the output of said circuits bing applied to a null indicator, wherein, in the case of an angular frequency $\omega = \omega_0$ of the wave, a zero measurement read on the indicator is obtained if the angle between the axis $O\xi$ or the axis $O\eta$ and the axis $Ox_2$ is zero, thus determining the orientation of the axis $O\xi$ to within 90°, wherein, after rotation of the probe through an angle of 45° and by varying the value of the angular frequency of the wave, the direction of variation on the null indicator gives the sign of the phase shift $\phi_0$ and the discrimination between slow axis and fast axis of the sample and the value $\phi_0$ is obtained from the values $\omega_0$ and $\omega_1$ at which the indicator is again at zero.

2. An acoustic polarimeter according to claim 1, wherein the high-frequency generator providing an angular frequency $\omega$ is frequency-modulated by a generator providing an angular frequency $\Omega$ and wherein the receiving circuit comprises an amplifier, the amplified signal being applied to a multiplier circuit which also receives the signal delivered by the generator providing an angular frequency $\Omega$ and wherein the signal produced at the output of the multiplier circuit is filtered by a low-pass filter connected to the zero indicator.

3. An acoustic polarimeter according to claim 1 or claim 2, wherein the length of the birefringent measuring plate is such as to introduce a phase shift $\Phi_0$ equal to an odd whole number of $\pi$ in the case of the high angular frequency $\omega_0$ which reduces the output signal to zero when no sample is present.

4. An acoustic polarimeter according to claim 1 or claim 2, wherein the measuring probe is mounted in a support which permits rotation of said probe through an angle of at least 120° about its geometrical axis and has a cylindrical surface with an angular position reference mark.

5. An acoustic polarimeter according to claim 4, wherein the birefringent measuring plate which supports the transmitting transducer is mounted in a member whilst the support of the receiving transducer is mounted in another member, said two members being adapted to form part of the probe support and capable of relative displacement in a direction parallel to the axis Oz so as to permit measurements when the sample is present and when said sample is not present.

6. An acoustic polarimeter according to claim 4, wherein the receiving transducer is rigidly fixed to the same face of the birefringent plate as the transmitting transducer, the polarimeter being intended to operate in reflection from the exit face of the sample.

7. An acoustic polarimeter according to claim 6, wherein the receiving transducer coincides with the transmitting transducer.

8. A polarimeter according to claim 1, wherein the birefringent plate is formed of material from the group consisting of quartz, ferroelectric ceramics and drawn metals.

9. A polarimeter according to claim 1, wherein the high-frequency generator comprises a chopper amplifier.

* * * * *